US005682690A

United States Patent [19]

Chang

[11] Patent Number: 5,682,690

[45] Date of Patent: Nov. 4, 1997

[54] FOOTWEAR WITH ADJUSTABLE MASSAGE UNITS

[76] Inventor: Shyh-Chye Chang, No. 19, Lun-Nan-I Rd., Tou-Liu City, Yun-Lin Hsien, Taiwan

[21] Appl. No.: 674,724

[22] Filed: Jul. 2, 1996

[51] Int. Cl.[6] .............. A61F 5/14; A43B 3/12

[52] U.S. Cl. .............. 36/141; 36/11.5

[58] Field of Search .............. 36/3 B, 11.5, 141, 36/27, 43, 44

[56] References Cited

U.S. PATENT DOCUMENTS

| | | | |
|---|---|---|---|
| 4,047,310 | 9/1977 | Sunoo | 36/141 X |
| 4,598,484 | 7/1986 | Ma | 36/3 R |
| 5,212,878 | 5/1993 | Burke et al. | 36/27 |
| 5,502,901 | 4/1996 | Brown | 36/27 X |
| 5,511,324 | 4/1996 | Smith | 36/27 |

FOREIGN PATENT DOCUMENTS

| | | | |
|---|---|---|---|
| 2916410 | 11/1976 | Germany | 36/11.5 |
| 6070801 | 3/1994 | Japan | 36/11.5 |
| 0661846 | 8/1987 | Switzerland | 36/141 |

*Primary Examiner*—B. Dayoan
*Attorney, Agent, or Firm*—Foley & Lardner

[57] ABSTRACT

A footwear item includes an elongated sole member, fastening device, and a plurality of spring-loaded massage rods. The sole member includes an upper sole formed with a plurality of upright holes, a lower sole, and a midsole sandwiched between the upper and lower soles. The midsole has a plurality of corresponding chambers that communicate with the upright holes respectively. The fastening device fastens the sole member to a wearer's foot after the wearer has stepped onto the upper sole of the sole member. Each of the massage rods has a lower end retained in the corresponding chamber, and an upper end which extends through the corresponding upright hole and outwardly of the upper sole. The upper end of the spring-loaded rod is depressed downwards against biasing action by the wearer's foot so as to provide massage effects thereto. The magnitude of massage force resulting from the massage rods can be selectively adjusted so as to suit any individual needs.

9 Claims, 6 Drawing Sheets

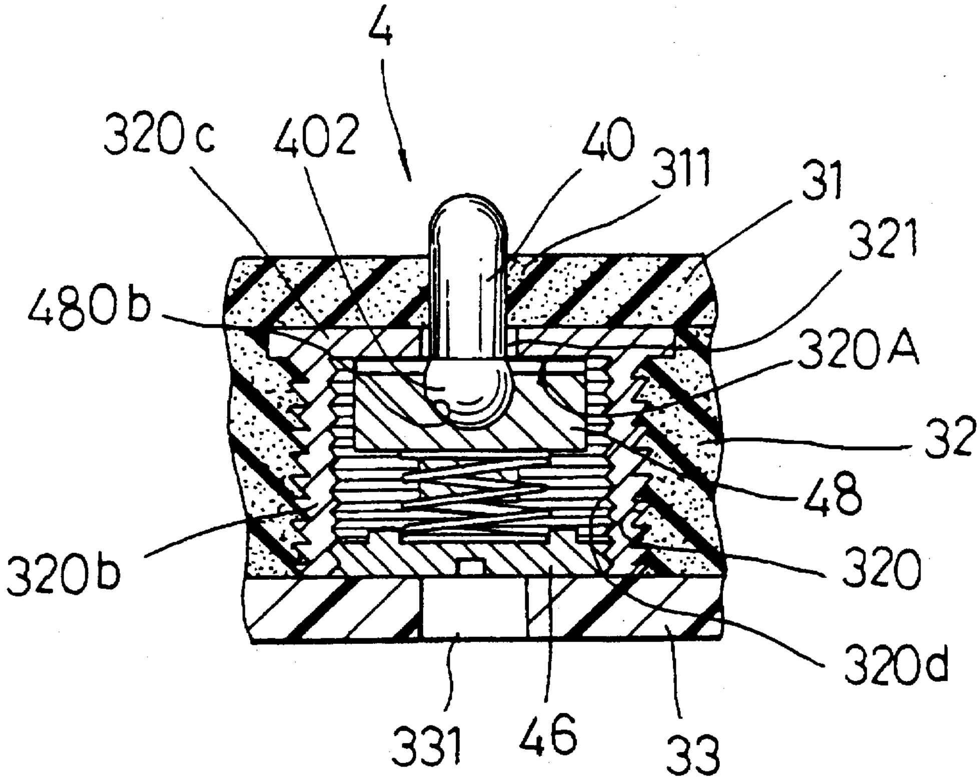
FIG . 3
FIG . 4
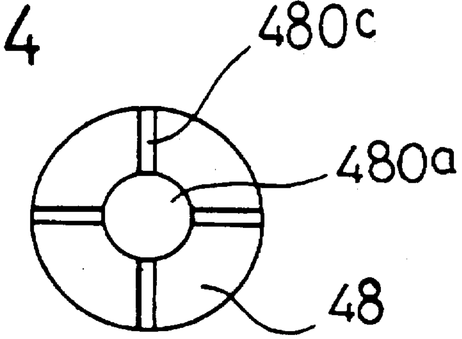

FOOTWEAR WITH ADJUSTABLE MASSAGE UNITS

BACKGROUND OF THE INVENTION

1. Field of the Invention

The invention relates to footwear, more particularly to footwear with a plurality of massage units attached thereto so as to provide massage effects to the wearer.

2. Description of the Related Art

Some footwear are provided with massaging sticks which project upwardly from the upper soles thereof to provide massage effects to the wearer's feet.

A drawback of the above-mentioned footwear is that the massaging force resulting from the massaging sticks cannot be varied and therefore are not suitable for every wearer.

SUMMARY OF THE INVENTION

The object of this invention is to provide footwear formed with a plurality of massage units the massaging force of which can be varied in order to suit each individual.

Accordingly, the footwear of this invention includes an elongated sole member, fastening means, and a plurality of spring-loaded massage rods. The sole member includes an upper sole formed with a plurality of upright holes, a lower sole, and a midsole sandwiched between the upper and lower soles. The midsole has a plurality of corresponding chambers that communicate with the upright holes respectively. The fastening means fasten the sole member to a wearer's foot after the wearer has stepped onto the upper sole of the sole member. Each of the massage rods has a lower end retained in the corresponding chamber, and an upper end which extends through the corresponding upright hole and outwardly of the upper sole. When the upper end of the spring-loaded rod is depressed downwards against biasing action by the wearer's foot, massage effects are provided thereto. The magnitude of massage force resulting from the massage rods can be adjusted so as to suit individual needs.

BRIEF DESCRIPTION OF THE DRAWINGS

Other features and advantages of this invention will become apparent in the following detailed description of the preferred embodiments of this invention, with reference to the accompanying drawings, in which:

FIG. 3 is an enlarged view of the circle A shown in FIG. 2;

FIG. 4 is a top view of a retaining member employed in the footwear of this invention;

DETAILED DESCRIPTION OF THE PREFERRED EMBODIMENTS

Figure 1:
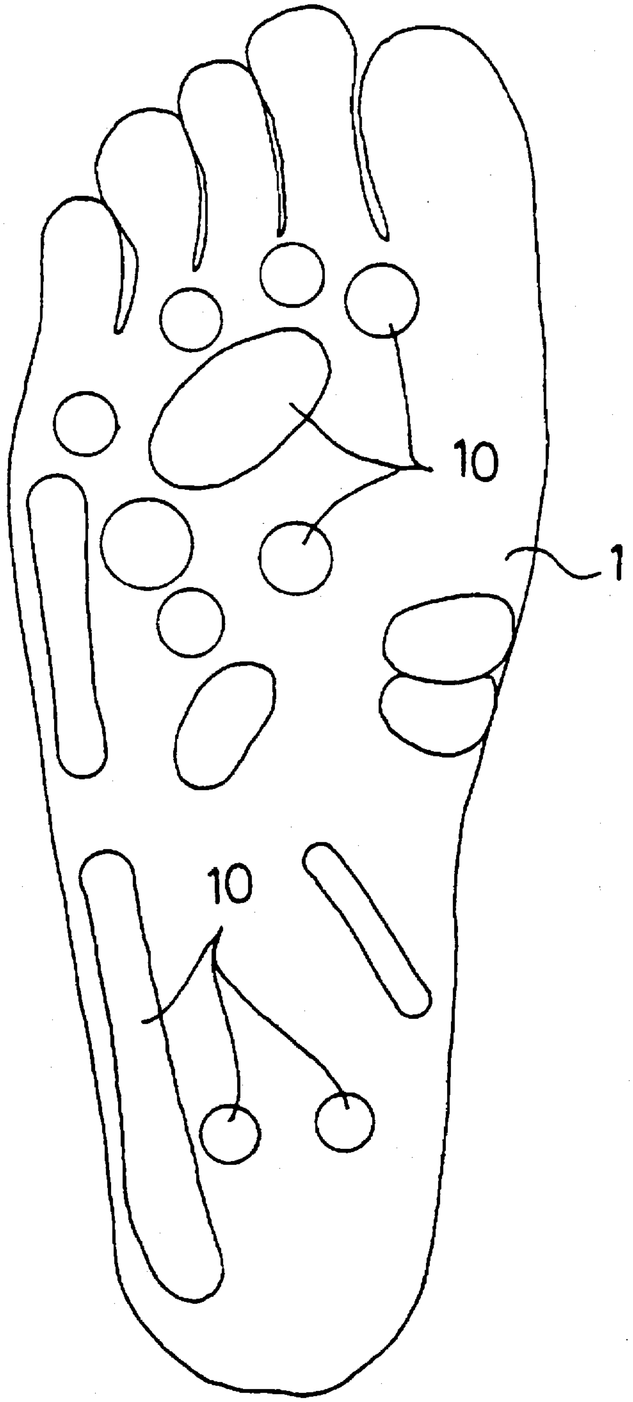
FIG. 1 is a bottom view of the human foot, illustrating some vital spots for pressure to be applied upon which can achieve massage effects.
Figure 2:
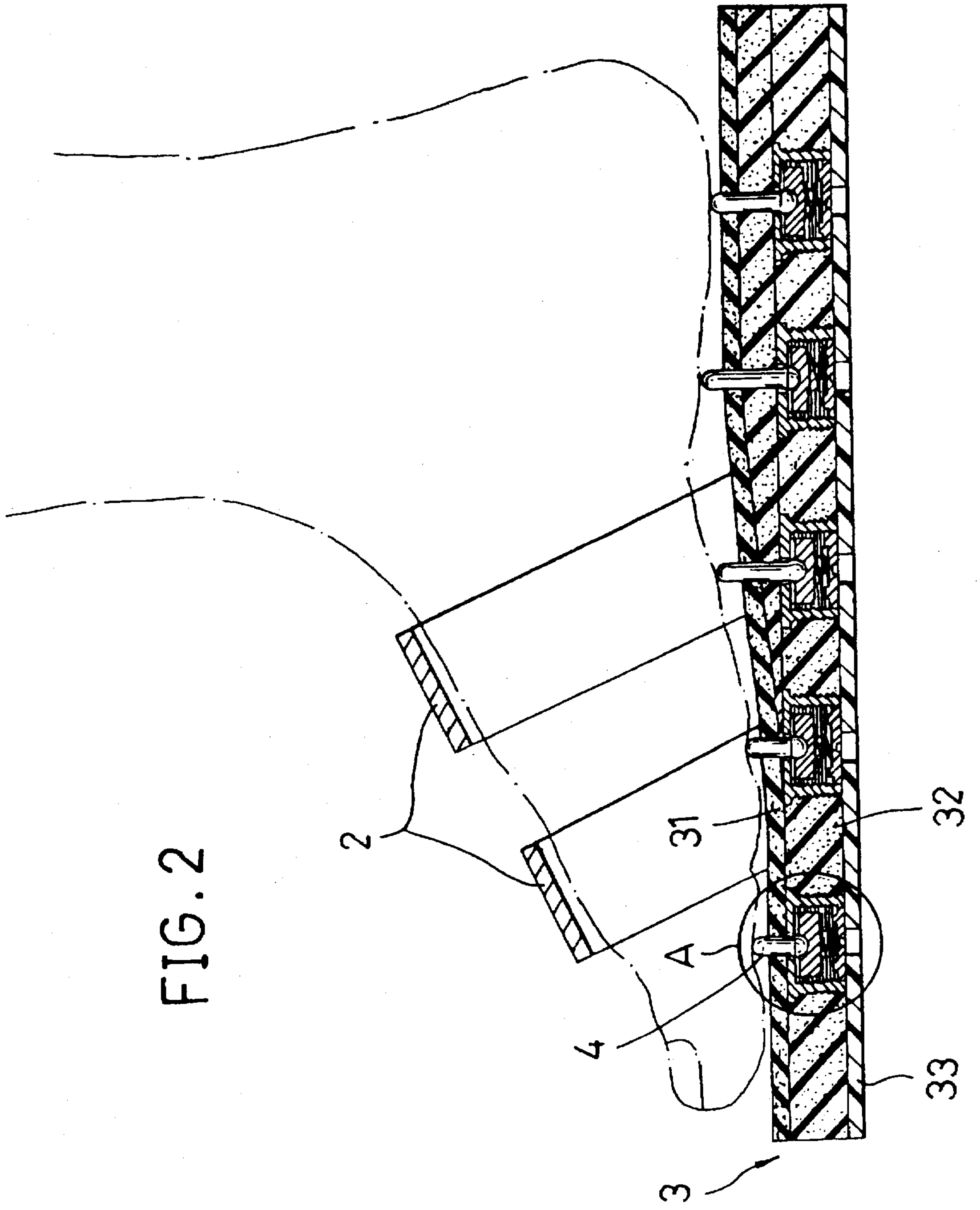
FIG. 2 is a sectional view of a footwear item of this invention being worn on a foot.

Referring to FIGS. 2 and 3, the preferred embodiment of a footwear item of this invention is shown to include an elongated sole member 3, fastening means 2, and a plurality of massage units 4 each of which includes a spring-loaded massage rod 40 with a predetermined biasing action.

As illustrated the sole member 3 includes an upper sole 31 formed with a plurality of upright holes 311, a lower sole 33, and a midsole 32 sandwiched between the upper and lower soles 31, 33. The midsole 32 has a plurality of spaced internal walls which define a corresponding number of chambers 320 that communicate with the upright holes 311 respectively. The fastening means 2 include a plurality of laces each of which has two opposite ends transversely fixed to the sole member 3 such that after the wearer has stepped onto the upper sole 31 of the sole member 3, the laces can be fastened on the wearer foot.

The midsole 32 is generally made of an elastomeric material and includes a plurality of plastic frame supports 320A disposed in the chambers 320 respectively to provide integrity thereto when the spring-loaded massage rod 40 is depressed. The frame support 320A is generally T-shaped and includes an upper wall **320*c* which has a through-hole 321 formed therethrough aligned with the corresponding upright hole 311 of the upper sole 31, and a lower portion 320*b* threaded to the bottom of the chamber 320. The frame support 320A further has an inner cylindrical wall 320*d* which is disposed between the upper wall 320*c* and the bottom of the chamber 320 and which has an inner threaded surface to engage by threading the outer circumferential wall of an adjusting member 46. A plastic retaining member 48 is disposed within the chamber 320 to couple with the lower end 402 of the spring-loaded massage rod 40 so as to abut against a lower surface of the upper wall 320*c* by the biasing action to retain the lower end 420 of the massage rod 40 in the chamber 320. When the upper end of the spring-loaded 40 rod is depressed downwards against the biasing action, massage effects are achieved on the wearer's foot. The magnitude of biasing action, that is, the massage force, resulting from each massage rod 40** can be adjusted in order to suit any individual needs.

Note that in the preferred embodiment, a ball-and-sock joint mechanism is interposed between the lower end 420 of the spring-loaded massage rod 40 and the retaining member 48. As shown in FIG. 4, the joint mechanism consists of a socket **480*a* disposed on the retaining member 48 and a ball 480*b* (see FIG. 3) integrally formed at the lower end 402 of the massage rod 40. The retaining member 48 has four radial grooves 480*c* formed on the upper surface thereof and communicated with an interior wall which defines the socket 480*a* and abuts against the ball 480*b* (see FIG. 3) so as to provide a cushioning effect to the ball 480*a* even when the spring-loaded massage rod 40 is depressed in a slightly inclined direction relative to an axis of the rod 40**.

Referring again to FIG. 3, the lower sole 33 has a corresponding number of apertures 331 formed therethrough for the extension of an adjustment tool (not shown) to actuate the adjusting member 46. The adjusting member 46 is movable relative to the frame support 320A in an axial direction of the spring-loaded massage rod 40 so as to regulate the biasing force of the spring such that the footwear of this invention can suit each individual.

Figure 5:
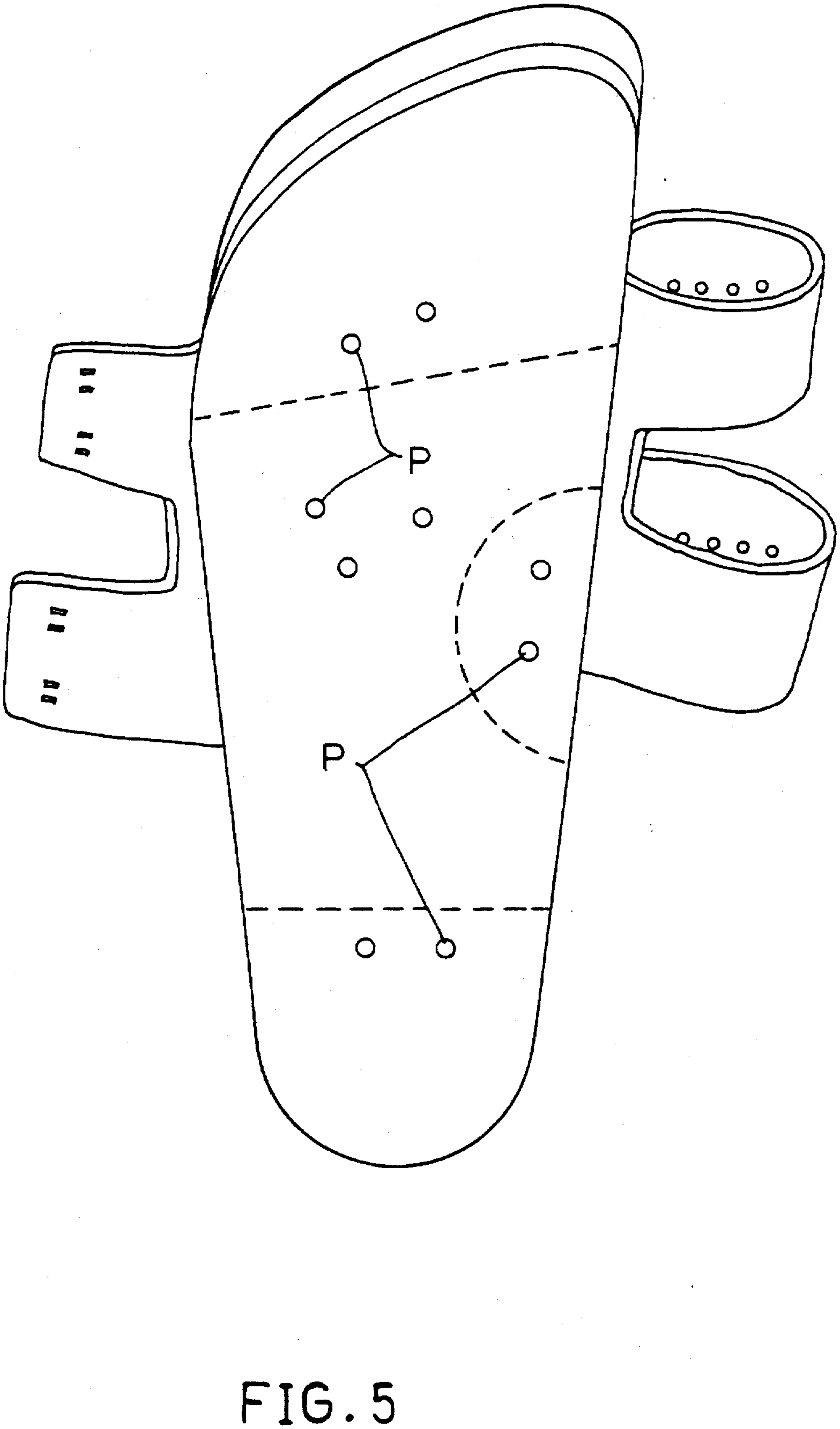
FIG. 5 is a top view of the footwear of this invention, illustrating positions of massage units.
Figure 6:
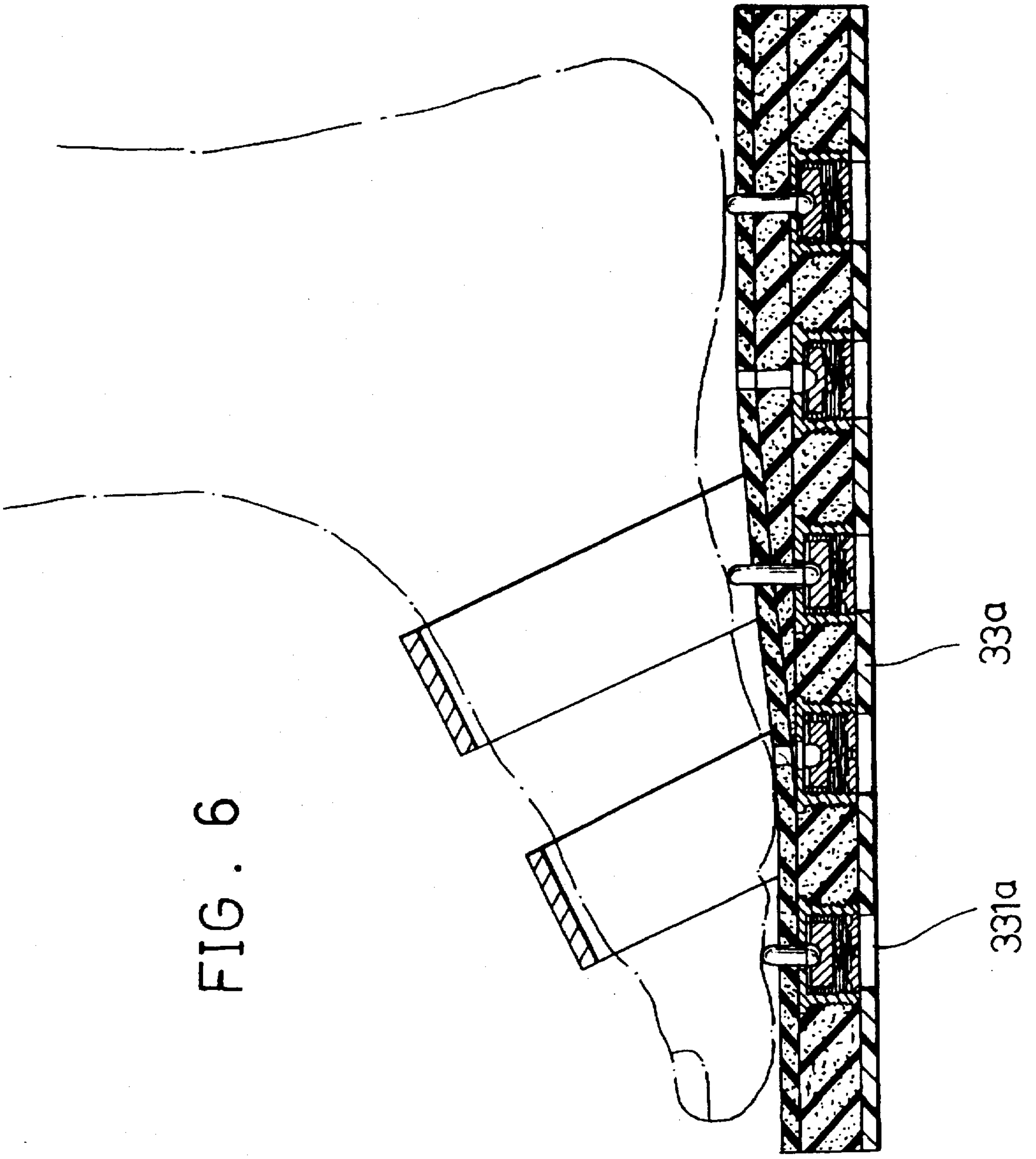
FIG. 6 is a sectional view of the footwear of this invention, illustrating where the massage rods can be removed in order to suit the wearer.

Other important aspect of the footwear is as follows:

As illustrated in FIGS. 5 and 6, the aperture **331*a* in the lower sole 33*a*** of the sole member can be constructed to be equivalent to the inner diameter of the frame support so that when the wearer of the footwear item does not require the massage effect from any of the spots P, the corresponding massage rods can be removed therefrom.

Figure 7:
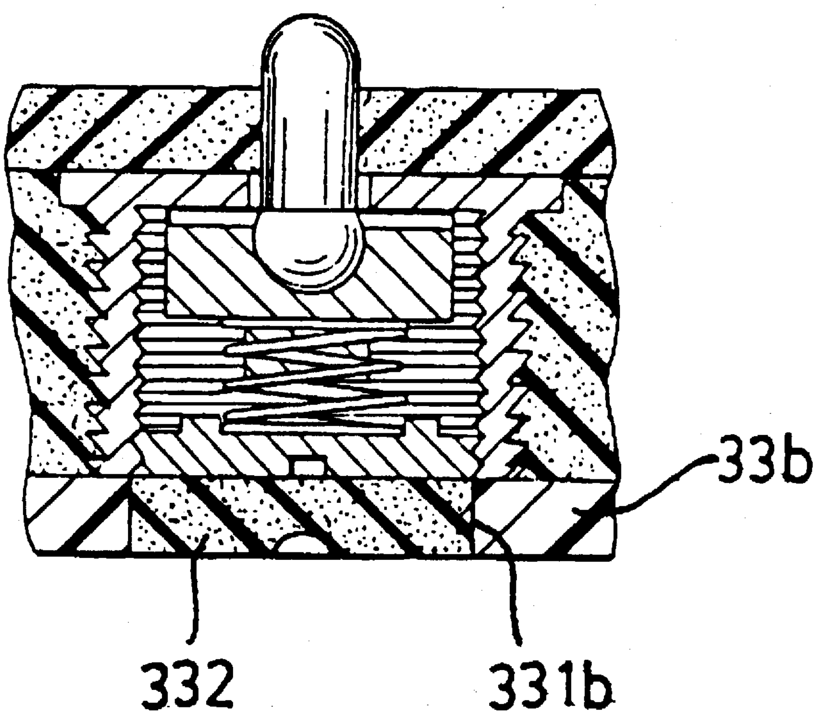
FIG. 7 is a partial sectional view of a modified footwear item of this invention.

As shown in FIG. 7, a plastic seal 332 can be press fitted into the aperture **331*b* of the lower sole 33** in order to prevent accidental movement of the adjustment member in the corresponding chamber.

With this invention thus explained, it is apparent that numerous modifications and variations can be made without departing from the scope and spirit of this invention. It is therefore intended that this invention be limited only as indicated in the appended claims.

I claim:

1. A footwear comprising:

an elongated sole member including an upper sole having a plurality of upright holes, a lower sole, and a midsole sandwiched between said upper and lower soles, said midsole being made of an elastomeric material and having a plurality of corresponding chambers communicated with said plurality of upright holes respectively;

means for fastening said sole member to a wearer's foot after a wearer has stepped onto said upper sole of said sole member;

a plurality of spring-loaded massage rods with different biasing actions, each having a lower end retained in said corresponding chamber, and an upper end extending through said corresponding upright hole and outwardly of said upper sole, whereby said upper end of each spring-loaded rod is depressed downwards against biasing action of said spring by the wearer's foot so as to provide a massage effect thereto;

a frame support disposed in said chamber to provide integrity thereto when said spring-loaded massage rod is depressed, said frame support including an upper wall which has a through-hole aligned with said upright hole;

a retaining member disposed within said chamber to couple with said lower end of said spring-loaded massage rod so as to abut against a lower surface of said upper wall by said biasing action to retain said lower end of said massage rod in said chamber; and a ball-and-sock joint mechanism interposed between said lower end of spring-loaded massage rod and said retaining member so as to permit a slightly inclined direction of movement of said spring-loaded massage rod when depressed.

2. The footwear according to claim 1, further comprising a spring force adjusting member disposed at the bottom of said chamber to urge said spring toward said lower end of said spring-loaded massage rod, and externally accessible for adjustment, said adjusting member being movable relative to said frame support in an axial direction of said spring-loaded massage rod so as to regulate biasing force of said spring.

3. The footwear according to claim 2, wherein said frame support includes an inner cylindrical wall between said upper wall of said support frame and said bottom of said chamber, having an inner threaded surface; and said adjusting member having a threaded surface on an outer circumferential wall thereof to match said inner threaded surface so as to screw said adjusting member upwards and downwards relative to said inner cylindrical wall.

4. A footwear according to claim 1, wherein said ball-and-socket joint mechanism includes a socket disposed on said retaining member and a ball at said lower end of said massage rod, and said retaining member is made of a plastic material and includes a radial groove that communicates with an interior wall which defines said socket and abuts against said ball so as to provide a cushioning effect to said ball even when said spring-loaded massage rod is depressed in a slightly inclined direction.

5. The footwear according to claim 3, wherein said lower sole has an aperture formed therethrough for extension of an adjustment tool to actuate said adjusting member upwards and downwards so as to vary said biasing action.

6. A footwear comprising:

an elongated sole member including an upper sole portion having a plurality of upright holes, a lower sole portion, and a midsole portion sandwiched between said upper and lower sole portions, said midsole portion having a plurality of corresponding chambers communicated with said plurality of upright holes respectively; and a plurality of spring-loaded massage rods, having springs each with ends that are adjustable in an axial direction relative to the massage rods to adjust the biasing action thereof, each of said rods having a lower end retained in said corresponding chamber and an upper end extending through said corresponding upright hole and outwardly of said upper sole portion, the upper ends of said spring-loaded rods being adapted to be depressed downwards by a wearer's foot against biasing action of said spring-loaded rods.

7. The footwear according to claim 6, further comprising a frame support disposed in said chamber to provide integrity thereto when said spring-loaded massage rod is depressed, said frame support including an upper wall which has a through-hole aligned with said upright hole.

8. The footwear according to claim 7, further comprising a spring force adjusting member disposed at the bottom of said chamber to urge said spring toward said lower end of said spring-loaded massage rod, and externally accessible for adjustment, said adjusting member being movable relative to said frame support in an axial direction of said spring-loaded massage rod so as to regulate biasing force of said spring.

9. The footwear according to claim 8, wherein said frame support includes an inner cylindrical wall between said upper wall of said support frame and said bottom of said chamber, having an inner threaded surface, said adjusting member having a threaded surface on an outer circumferential wall thereof to match said inner threaded surface so as to screw said adjusting member upwards and downwards relative to said inner cylindrical wall.

* * * * *